United States Patent
Larose et al.

(10) Patent No.: US 11,364,374 B2
(45) Date of Patent: Jun. 21, 2022

(54) FLANGED HEART TISSUE BLOCKER

(71) Applicant: HeartWare, Inc., Miami Lakes, FL (US)

(72) Inventors: Jeffrey A. Larose, Raleigh, NC (US); Lance Lynn Andrus, Southborough, MA (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 16/032,514

(22) Filed: Jul. 11, 2018

(65) Prior Publication Data

US 2018/0318480 A1    Nov. 8, 2018

Related U.S. Application Data

(62) Division of application No. 15/471,575, filed on Mar. 28, 2017, now Pat. No. 10,159,772.

(60) Provisional application No. 62/315,260, filed on Mar. 30, 2016.

(51) Int. Cl.
*A61M 60/857* (2021.01)
*A61B 17/02* (2006.01)

(52) U.S. Cl.
CPC ........... *A61M 60/857* (2021.01); *A61B 17/02* (2013.01); *A61B 2017/0243* (2013.01)

(58) Field of Classification Search
CPC .................................................. A61M 1/1008
See application file for complete search history.

(56) References Cited

U.S. PATENT DOCUMENTS

| | | | |
|---|---|---|---|
| 3,818,511 A | 6/1974 | Goldberg et al. | |
| 4,650,486 A | 3/1987 | Chareire | |
| 5,084,064 A | 1/1992 | Barak et al. | |
| 5,578,353 A * | 11/1996 | Drew, III | B44C 1/175 283/58 |
| 5,810,708 A * | 9/1998 | Woodard | A61M 1/3659 600/16 |

(Continued)

FOREIGN PATENT DOCUMENTS

| CN | 102395331 A | 3/2012 |
|---|---|---|
| WO | 0015275 A2 | 3/2000 |

(Continued)

OTHER PUBLICATIONS

International Search Report and Written Opinion dated Jun. 16, 2017, for corresponding International Application No. PCT/US2017/024501, International Filing Date: Mar. 28, 2017 consisting of 10-pages.

(Continued)

*Primary Examiner* — Jacqueline Woznicki
(74) *Attorney, Agent, or Firm* — Shumaker & Sieffert, P.A.

(57) ABSTRACT

An apparatus for protecting heart tissue from an implanted inlet element of a blood pump. The apparatus includes a flange member having a first radially constricted configuration and a second radially expanded configuration, the flange member being biased in its second radially expanded configuration. The flange member defines an opening there through sized to receiving the inlet element of the blood pump. A retaining element extending from the flange member is included, the retaining element being flexible and sized to be disposed about at least a portion of the inlet element.

20 Claims, 9 Drawing Sheets

(56) References Cited

U.S. PATENT DOCUMENTS

| | | | |
|---|---|---|---|
| 5,948,019 A | 9/1999 | Shu et al. | |
| 6,001,056 A * | 12/1999 | Jassawalla | A61F 2/2412 600/16 |
| 6,048,309 A * | 4/2000 | Flom | A61B 17/0293 600/206 |
| 6,076,529 A | 6/2000 | Vanney et al. | |
| 6,200,280 B1 * | 3/2001 | Brenneman | A61H 31/007 601/41 |
| 6,287,267 B1 * | 9/2001 | Brenneman | A61H 31/007 601/107 |
| 6,290,639 B1 * | 9/2001 | Mussivand | A61M 1/1037 600/16 |
| 6,346,071 B1 * | 2/2002 | Mussivand | A61M 1/1008 600/16 |
| 6,688,861 B2 | 2/2004 | Wampler | |
| 6,726,660 B2 * | 4/2004 | Hessel | A61F 5/445 604/175 |
| 7,575,423 B2 | 8/2009 | Wampler | |
| 7,744,527 B2 | 6/2010 | Cohn | |
| 7,976,271 B2 | 7/2011 | LaRose et al. | |
| 8,007,254 B2 | 8/2011 | LaRose et al. | |
| 8,419,609 B2 | 4/2013 | Shambaugh, Jr. et al. | |
| 9,283,314 B2 | 3/2016 | Prasad et al. | |
| 9,381,286 B2 | 7/2016 | Spence et al. | |
| 9,440,013 B2 | 9/2016 | Dowling et al. | |
| 9,744,279 B2 | 8/2017 | Tamez et al. | |
| 2002/0095210 A1 * | 7/2002 | Finnegan | A61F 2/064 623/3.26 |
| 2002/0103495 A1 | 8/2002 | Cole | |
| 2003/0023255 A1 * | 1/2003 | Miles | A61M 1/10 606/158 |
| 2003/0176911 A1 * | 9/2003 | Iancea | A61F 2/915 623/1.13 |
| 2004/0054251 A1 * | 3/2004 | Liotta | A61M 1/1037 600/17 |
| 2004/0116945 A1 | 6/2004 | Sharkawy et al. | |
| 2004/0122397 A1 * | 6/2004 | Morman | A61F 13/15723 604/385.01 |
| 2004/0147803 A1 * | 7/2004 | Hegde | A61M 1/1067 600/16 |
| 2004/0171905 A1 | 9/2004 | Yu et al. | |
| 2005/0119637 A1 * | 6/2005 | Lundgren | A61M 39/0247 604/539 |
| 2006/0167333 A1 * | 7/2006 | Moore | A61M 1/10 600/16 |
| 2006/0235357 A1 * | 10/2006 | Woodward | A61M 1/10 604/264 |
| 2007/0106315 A1 | 5/2007 | Gregoric et al. | |
| 2007/0134993 A1 | 6/2007 | Tamez et al. | |
| 2007/0283607 A1 * | 12/2007 | Sloot | G09F 3/005 40/633 |
| 2008/0009668 A1 | 1/2008 | Cohn | |
| 2008/0009887 A1 | 1/2008 | Cohn | |
| 2008/0087680 A1 * | 4/2008 | Amundson | A47K 10/38 221/150 R |
| 2008/0236011 A1 * | 10/2008 | Bekker | A61B 90/90 40/633 |
| 2010/0082099 A1 | 4/2010 | Vodermayer et al. | |
| 2010/0106171 A1 | 4/2010 | Arepally et al. | |
| 2011/0118766 A1 * | 5/2011 | Reichenbach | A61M 1/10 606/153 |
| 2011/0118829 A1 * | 5/2011 | Hoarau | A61M 1/10 623/2.11 |
| 2011/0118833 A1 * | 5/2011 | Reichenbach | A61B 17/11 623/3.1 |
| 2011/0251450 A1 * | 10/2011 | Pagani | A61B 17/3478 600/16 |
| 2012/0059212 A1 | 3/2012 | Larose et al. | |
| 2012/0095281 A1 | 4/2012 | Reichenbach et al. | |
| 2012/0143141 A1 * | 6/2012 | Verkaik | A61M 1/10 604/175 |
| 2012/0296151 A1 * | 11/2012 | Curtis | A61B 17/320016 600/16 |
| 2012/0296358 A1 * | 11/2012 | Nguyen | A61B 17/11 606/170 |
| 2015/0038770 A1 * | 2/2015 | Colella | A61M 1/122 600/16 |
| 2015/0112120 A1 | 4/2015 | Andrus | |
| 2015/0359952 A1 | 12/2015 | Andrus et al. | |
| 2015/0364863 A1 | 12/2015 | Andrus et al. | |
| 2015/0367048 A1 | 12/2015 | Brown et al. | |
| 2016/0067395 A1 | 3/2016 | Jimenez et al. | |
| 2016/0375186 A1 * | 12/2016 | Tuseth | A61B 17/3468 600/16 |
| 2017/0173236 A1 | 6/2017 | Andrus | |
| 2017/0189060 A1 | 7/2017 | Andrus | |
| 2017/0281840 A1 | 10/2017 | LaRose et al. | |
| 2017/0326280 A1 | 11/2017 | Tamez et al. | |
| 2019/0046701 A1 * | 2/2019 | Kallenbach | A61M 1/3659 |

FOREIGN PATENT DOCUMENTS

| | | |
|---|---|---|
| WO | 108190 A1 | 12/2004 |
| WO | 2004108190 A1 | 12/2004 |
| WO | 2007047933 A2 | 4/2007 |
| WO | 2006121855 A3 | 11/2008 |
| WO | 2012018917 A1 | 2/2012 |
| WO | 2015017388 A1 | 2/2015 |

OTHER PUBLICATIONS

China National Intellectual Property Administration, Notice of the First Office Action and Search Report dated May 7, 2020, for corresponding Chinese Application No. 201780021992.8 consisting of 8 pages.

Prosecution History from U.S. Appl. No. 15/471,575, now issued U.S. Pat. No. 10,159,772, dated Mar. 28, 2017 through Dec. 14, 2021, 323 pp.

* cited by examiner

FLANGED HEART TISSUE BLOCKER

CROSS-REFERENCE TO RELATED APPLICATION

This application is a divisional of patent application Ser. No. 15/471,575, filed Mar. 28, 2017, entitled FLANGED HEART TISSUE BLOCKER, and is related to and claims priority to U.S. Provisional Patent Application Ser. No. 62/315,260, filed Mar. 30, 2016, entitled FLANGED HEART TISSUE BLOCKER, the entirety of which is incorporated herein by reference.

STATEMENT REGARDING FEDERALLY SPONSORED RESEARCH OR DEVELOPMENT n/a

TECHNICAL FIELD

The present invention relates to components and methods used in connection with implanted heart devices, such as ventricular assist devices and other associated elements.

BACKGROUND

The heart is sometimes incapable of providing sufficient pumping capacity to meet the needs of the body. The effects of this inadequacy can be alleviated by providing a mechanical pump referred to as a mechanical circulatory support device ("MCSD"). An MCSD can be implanted to supplement the pumping action of the heart, most commonly for an extended period of time such as several years.

An MCSD is most commonly connected to the left ventricle. In this arrangement, an inlet end of the pump, or an inlet cannula connected to the inlet end of the pump, is implanted in the wall of the ventricle, such as at the apex of the ventricle. An outlet cannula is connected between the outlet end of the pump and an artery such as the aorta. MCSDs which are connected to a ventricle commonly are referred to as ventricular assist devices or "VADs." During operation, the MCSD assists the heart to pump blood from the left ventricle to the aorta.

MCSDs are typically connected to the heart through the use of a mounting element such as a mounting ring. In use of such a mounting ring, the mounting ring is secured to the outside of the heart by suturing or other fastening techniques. A separate surgical tool is used to core a hole in the heart within the ring. An inlet cannula or other inlet element of the MCSD may then be inserted through the hole into the heart. The mounting ring may then be tightened to secure the MCSD to the ring and thus secure the MCSD to the heart.

In some instances, the heart wall, thrombus disposed on the heart wall, or other tissues or deposits may be drawn into the inlet element. Tissues or deposits drawn into the inlet element may block the flow of blood into the inlet element and may cause other complications.

SUMMARY

The present invention advantageously provides an apparatus for protecting heart tissue from an implanted inlet element of a blood pump. The apparatus includes a flange member having a first radially constricted configuration and a second radially expanded configuration, the flange member being biased in its second radially expanded configuration. The flange member defines an opening there through sized to receiving the inlet element of the blood pump. A retaining element extending from the flange member is included, the retaining element being flexible and sized to be disposed about at least a portion of the inlet element.

In another aspect on this embodiment, a mounting element is included configured for fastening to an exterior surface of the wall of the heart independently of the flange member and the retaining element, the mounting element being configured to retain the implanted inlet element in position relative to the heart, the retaining element being configured to engage the mounting element.

In another aspect on this embodiment, the mounting element defines a bore and is sized to receive the implanted inlet element and the retaining element within the bore.

In another aspect on this embodiment, the mounting element includes a clamp configured to constrict the bore and engage the retaining element between the implanted inlet element and the mounting element.

In another aspect on this embodiment, the retaining element defines a tubular body having a proximal end and a distal end, and wherein the tubular body defines an annular pocket distal to the distal end of the tubular body, and wherein the flange member includes a flexible washer disposed within the annular pocket.

In another aspect on this embodiment, the tubular body includes a plurality of perforation lines extending distally from the proximal end of the tubular body.

In another aspect on this embodiment, the retaining elements includes at least one from group consisting of a knitted material and polyester.

In another aspect on this embodiment, the flange member includes a plurality of radially disposed ribs, wherein the ribs are configured to bias the flange member in its radially expanded configuration.

In another aspect on this embodiment, the flange member includes a plurality of radially disposed apertures, the radially disposed apertures being sized to promote cardiac tissue ingrowth.

In another aspect on this embodiment, a flexible layer of material circumferentially disposed around a portion of the retaining element is included, the flexible layer of material configured to prevent seepage of blood from the heart into an interior of the retaining element.

In another embodiment, a method implanting an apparatus for protecting heart tissue from an implanted inlet element of a blood pump includes advancing a flange member in a radially constricted configuration through an opening of a heart wall, the flange member including a retaining element defining a tubular body extending proximally out of the heart through the opening, the flange member being configured to transition to a radially expanded configuration after passage through the opening of the heart wall. The flange member and the retaining element are positioned to overlie an interior surface of the heart wall surrounding the opening.

In another aspect of this embodiment, the method further includes mounting the inlet element of the blood pump to the heart, and wherein mounting of the inlet element of the blood pump further includes advancing the inlet element through the opening of the heart wall beyond the flange member.

In another aspect of this embodiment, mounting the inlet element includes fastening a mounting element on the exterior of the heart wall independently of the flange member.

In another aspect of this embodiment, mounting the inlet element further includes engaging the mounting element to retain the inlet element in position relative to the mounting member and to retain the retaining element in position relative to the mounting member.

In another aspect of this embodiment, fastening the mounting element to the heart is performed before advancing the flange member through the opening in the heart wall, and wherein the mounting element defines a bore, and wherein the flange member is advanced through the bore into the opening and the retaining element extends through the bore after advancement of the flange member through the opening.

In another aspect of this embodiment, engaging the mounting element includes constricting the bore of the mounting element to retain the retaining element between the inlet element and the bore of mounting element.

In another aspect of this embodiment, the method further includes separating a portion of the tubular body adjacent a proximal end of the tubular body remote from the flange member into strips and folding the strips outwardly from the tubular body.

In another aspect of this embodiment, advancing the flange member through the opening of the heart wall further includes placing the flange member within a guiding tube having an open distal end; advancing the open end of the guiding tube through the opening of the heart wall; and advancing the flange member through the open distal end of the guiding tube.

In another aspect of this embodiment, the flange member is resilient and biased in the radially expanded configuration.

In yet another embodiment, an apparatus for protecting heart tissue from an implanted inlet element of a blood pump includes a flange member having a first radially constricted configuration and a second radially expanded configuration, the flange member being biased in its second radially expanded configuration, the flange member defining an opening there through sized to receiving the inlet element of the blood pump, the flange member defining an annular pocket and including a flexible washer disposed within the pocket, the flexible washer including a plurality of radially disposed ribs and apertures. A retaining element extends proximally from the flange member, the retaining element being flexible and radially disposed about the opening, the retaining element defining a tubular body defining a plurality of tearable strips, the tubular body defining a lumen coaxial with the opening of the flange member.

BRIEF DESCRIPTION OF THE DRAWINGS

The present application will become better understood with regard to the following description and accompanying drawings in which.

DETAILED DESCRIPTION

Figure 1:
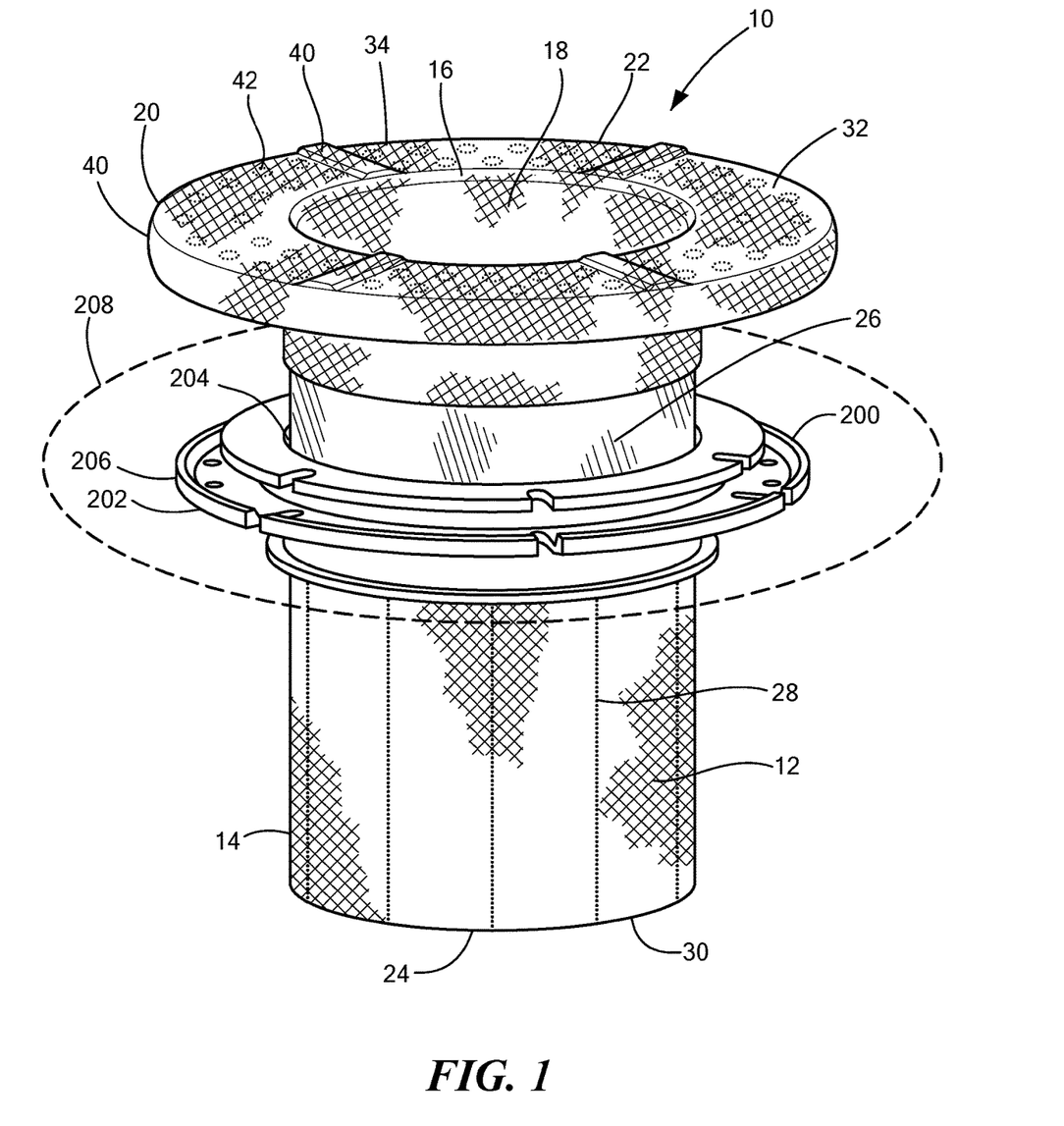
FIG. 1 is a perspective view of apparatus in accordance with one embodiment of the application.

Referring now to the drawings in which like designators refer to like elements, there is shown in FIG. 1 an apparatus for protecting heart tissue from an implanted inlet element of a blood pump constructed in accordance with the principles of the present application and designated generally as 100. The apparatus 100 may include a flange member 10 and a retaining element 12, which in one embodiment, define a hollow tubular body 14. The member 10 has an inner edge 16 that defines an opening 18 into the hollow tubular body 14. The flange member 10 also has an outer edge 20 that defines a radial extent of flange member 10. The tubular body 14 may be composed of a flexible material such as composed of one or more layers of a biocompatible fabric, plastic, or metal. For example, tubular body 14 may be composed of one or more composite layers of knitted polymers, such as polyethylene terephthalate ("PET").

Continuing to refer to FIG. 1, tubular body 14 has a distal end 22 and a proximal end 24. The tubular body 14 has interior diameter large enough to pass the inlet element of an MCSD as discussed below, typically on the order of 16-20 mm. In one configuration, the tubular body 14 is flexible but has sufficient stiffness to retain its shape so that it does not bend or close under the influence of gravity. A fabric may be provided with a medically acceptable coating such as a lacquer to increase its stiffness. For example, the retaining element 12 may include a flexible layer of material 26, for example, silicone, impregnated within the fabric that defines the retaining element 12 or otherwise is circumferentially disposed around a portion of the retaining element 12. The flexible layer of material 26 is configured to prevent seepage of blood from the heart into an interior of the retaining element 12. In one configuration, the flexible layer of material 26 defines a height greater than the thickness of the heart well. Alternatively or additionally, the retaining element 12 may include multiple layers of fabric. A plurality of tear lines 28 may extend from the proximal end 24, at least of part of the distal to the distal end 22. The material of the tubular body 14 may be weakened along the tear lines 28, so as to allow at least a portion of tubular body 14 adjacent the proximal end 24 to be separated into teardown strips 30 during use, as further discussed below. For example, the material of the tubular body 14 may be perforated, scored or partially cut along the tear lines 28 during manufacture.

Figure 4:
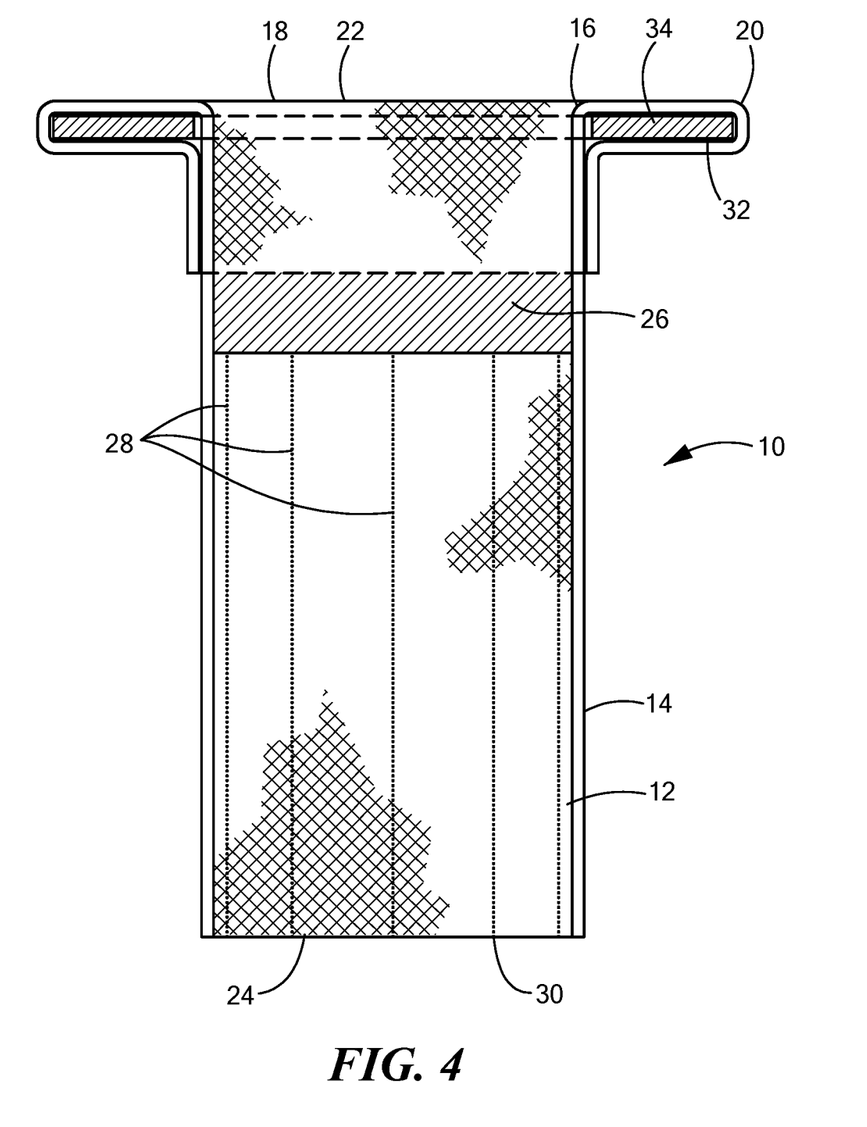
FIGS. 4 and 5 are diagrammatic cross-sectional views depicting portions of the apparatus of FIGS. 1 and 2.

The tubular body 14 includes an annular pocket 32 adjacent distal end 22 and distal to the tear lines 28. Annular pocket 32 extends around the tubular body 14. For example, where the tubular body 14 is formed from a textile, the annular pocket 32 may be manufactured on a tubular knitting machine so that the annular pocket 32 can be formed during manufacture, without stretching the material of the tubular body. In one configuration, the flange member 10 is composed of a flexible washer 34 that is disposed in the annular pocket 32 so that the flange member 10 includes both the flexible washer 34 and the material of the tubular body 14 forming the annular pocket 32. Flexible washer 34 may be composed of any number of flexible materials, including rubbers, polymers such as PET or silicone. Flexible washer 34 may have a thickness that allows for sufficient flexibility and radial constriction as discussed below. For example, the flexible washer 34 may have a thickness between 2 and 3 millimeters. Washer 34 may further include interior diameter equal to or slightly greater than the interior diameter of tubular body 14. During manufacture, flexible washer 34 may be positioned within annular pocket 32 while the annular pocket 34 is open as shown in FIG. 4. Once flexible washer 34 is positioned within the annular pocket 34, it optionally may be bonded or sewn into place. For example, where the tubular body 14 includes a portion projecting distally beyond the annular pocket 32, this portion may be folded back proximally within the tubular body 14 so as to cover the inner edge 16 of flexible washer 34. The folded flexible material may then be sewn or otherwise attached to the inside portion of tubular body 14, so as to maintain flexible washer 34 within annular pocket 32.

Continuing to refer to FIG. 1, a mounting ring 200 may be included and configured to engage at least a portion of the retaining element 12. The mounting ring 200 may a conventional mounting ring as, for example, the a mounting ring as disclosed in U.S. Published Patent Application Nos. 2004/0171905, 2007/0134993, and 2015/0112120, the disclosures of which are hereby incorporated by reference herein. The mounting ring has a body 202 with elements defining a bore 204 extending through the body 202, and also has features which can be used to attach the body 202 to the outside of the heart wall so that the bore 204 extends towards and away from the wall. In the example shown, the body 202 includes with a base plate 206 on a distal side of the ring 200 which faces toward the heart when the ring 200 is installed, and a ring of fabric schematically indicated in broken lines at 208 attached to the base plate 206 and encircling the body 202. A mounting ring 200 of this type can be secured in place by suturing the fabric ring to the exterior of the heart. Other mounting rings are equipped with barbs or other fasteners for attaching the body of the ring to the heart wall. The mounting ring is arranged so that a portion of the body defining at least part of the main bore 204 is compressible to constrict the bore 204 around an inlet element of the MCSD to hold the element in place. As shown, for example, in U.S. Published Patent Application No. 2007/0134993, the body 202 may include deformable elements such as a pair of generally C-shaped arms (not shown) on opposite sides of the bore 204, so that the bore 204 can be constricted by forcing the arms toward one another. The body 202 may also include an element referred to as a gimbal ring (not shown) defining all or part of bore 204, the gimbal ring be arranged to tilt through a limited range of motion relative to the base plate 206 to allow the inlet element of the to tilt relative to the base plate 206 during installation. The mounting ring 200 may further includes a clamp 210 (FIG. 6) configured to deform the body 202 so as to constrict the bore 204. A guiding tube 300 (FIG. 5) formed from a substantially rigid material such as a metal and having an outside diameter may be included and configured to fit within the bore 204 of the mounting ring 200 while the bore 204 is in an unconstructed state. Guiding tube 300 may include a thin wall and may further include a stop member 302 projecting outwardly adjacent a proximal end of the guiding tube 300. A pusher tube 304, also formed from a thin, rigid material, is slidably received within guiding tube 300. The pusher tube 304 may have a stop 306 projecting outwardly at its proximal end.

Figure 5:
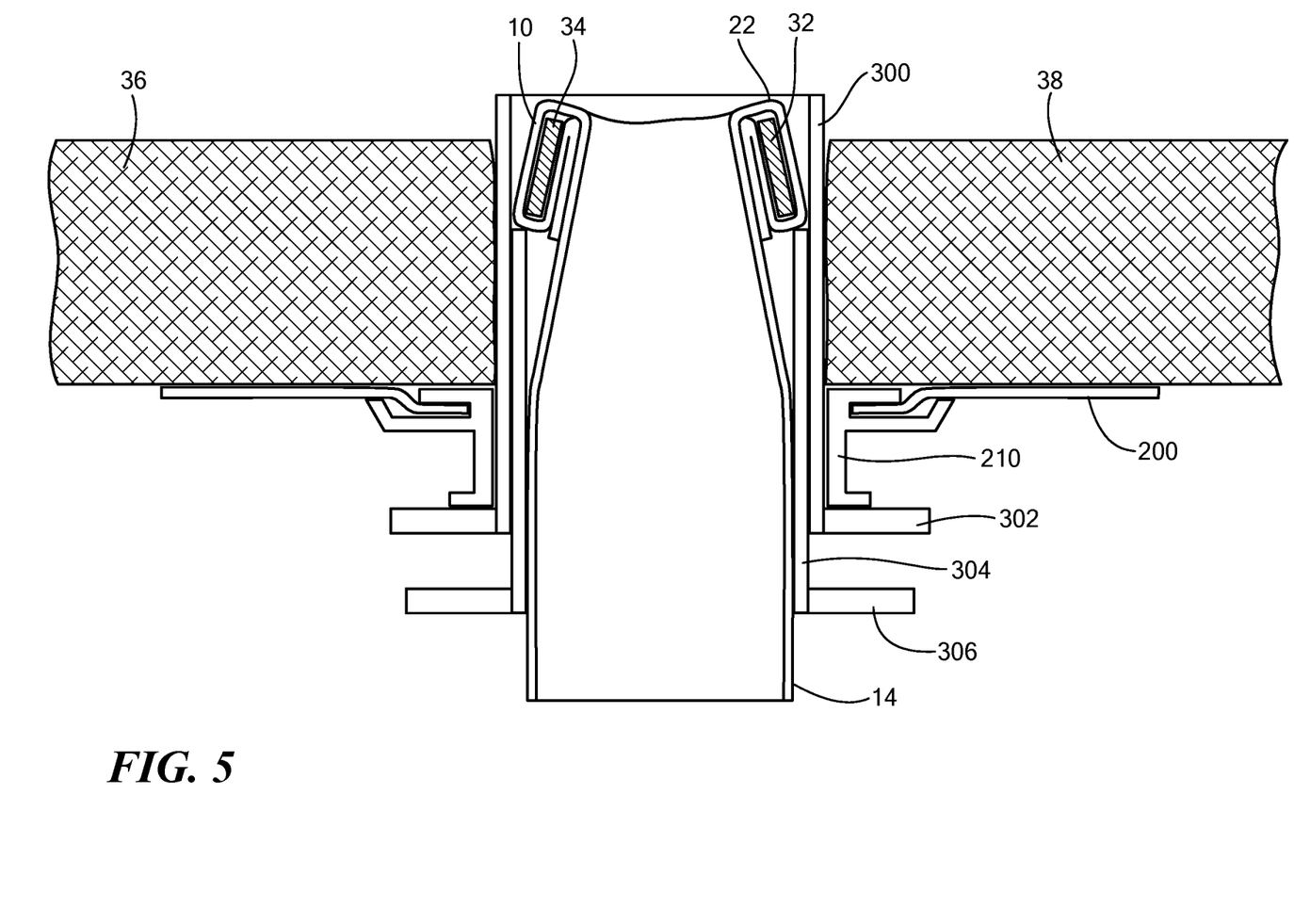
Figure 6:
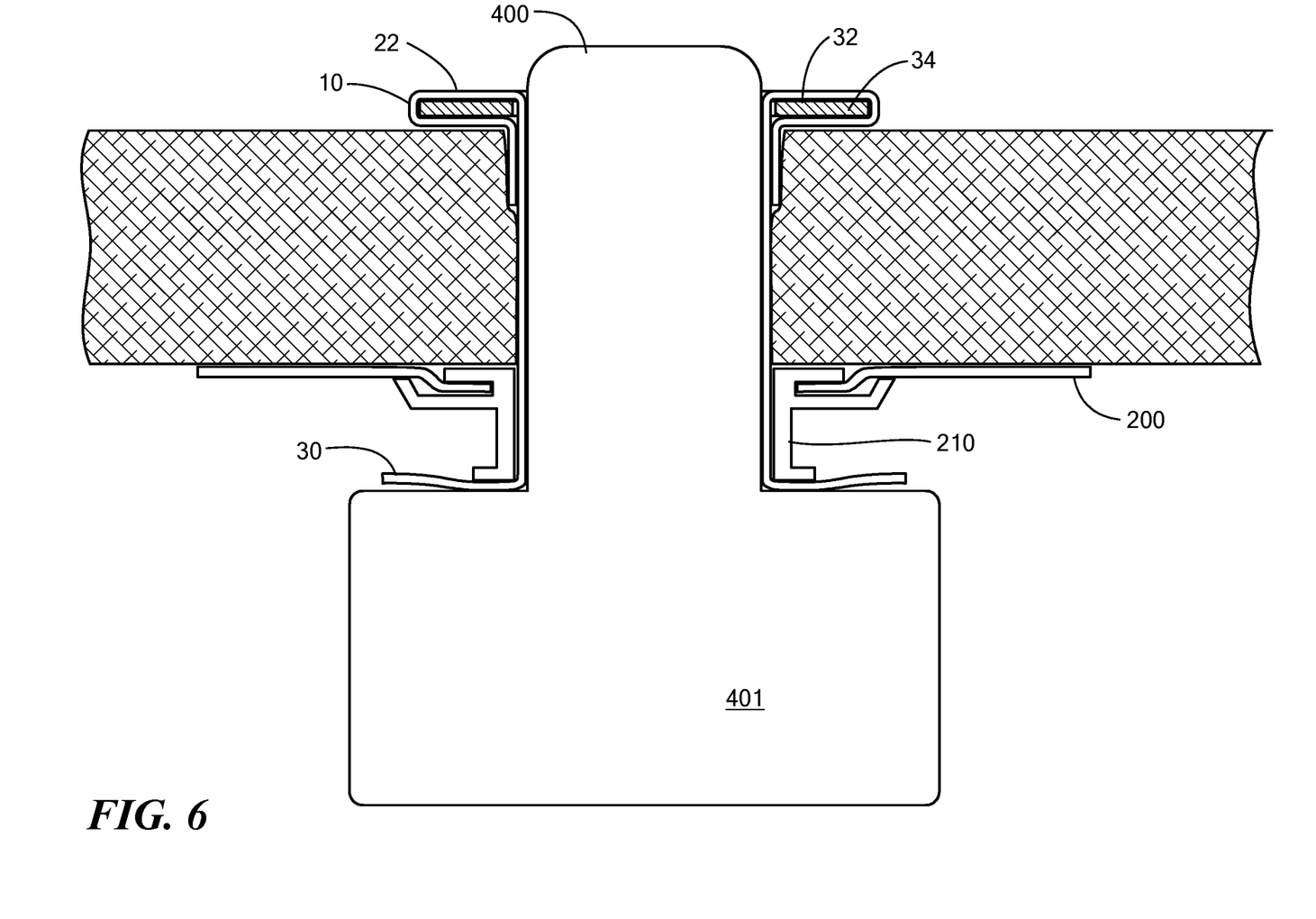
FIG. 6 is a view similar to FIGS. 4 and 5 but depicting the apparatus in conjunction with an MCSD.
Figure 8:
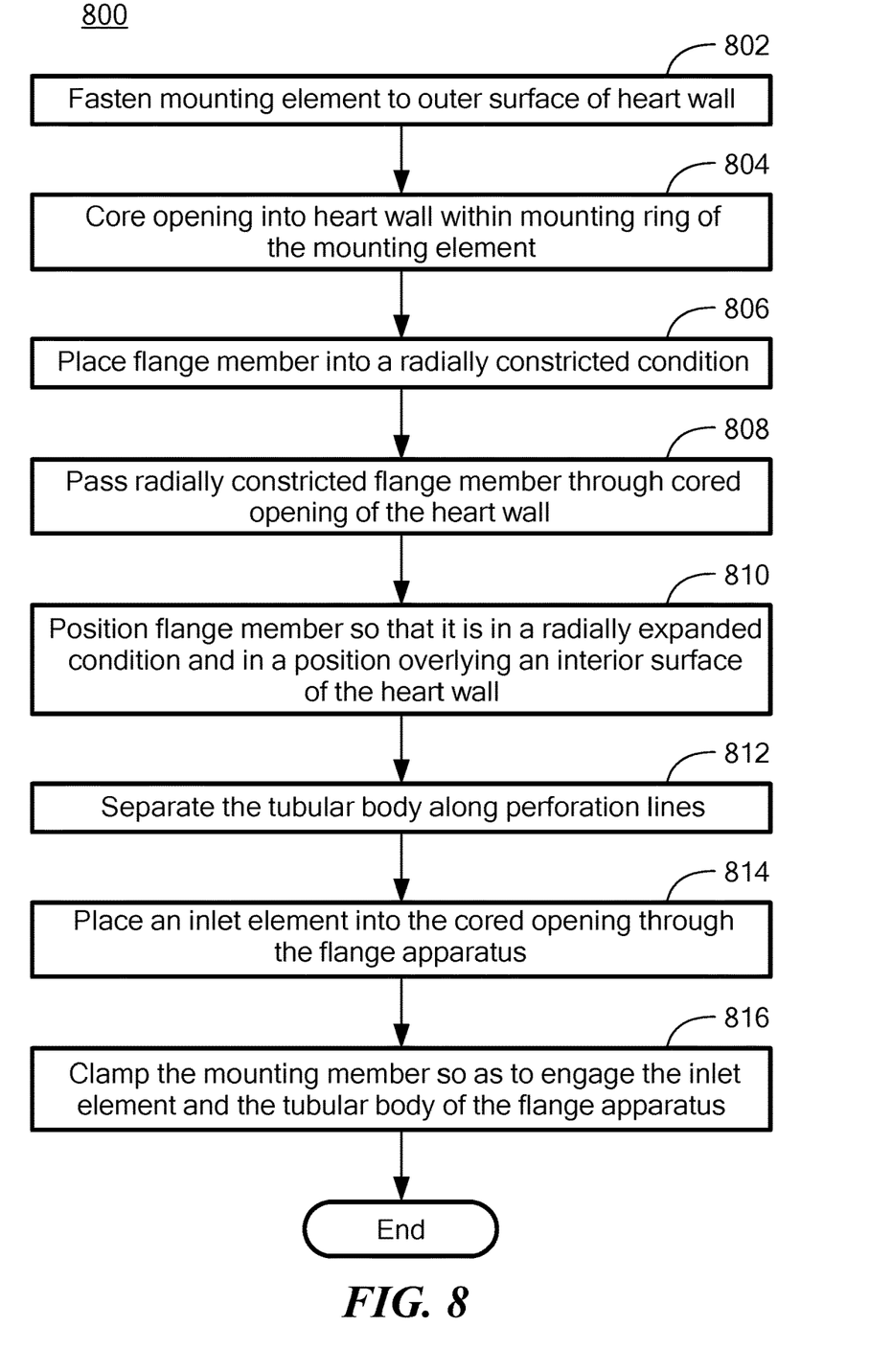
FIG. 8 is a flow diagram in accordance with aspects of the application.

In a method according to a further aspect of the disclosure, schematically depicted in the flow chart of FIG. 8, the mounting ring 200 may fixed to the to the outer surface 36 of heart wall 38 (FIG. 5), such as by suturing fabric ring 208 to the heart wall 38 (step 802). A coring tool (not shown) is used to form a hole in the heart wall 38 in alignment with the bore 204 of the mounting ring 200 (step 804). The flange member 10 may be deformed from a second radially expanded configuration in which the flange member is biased in a radially expanded configuration or condition (depicted in FIGS. 1-4) to a first radially constricted configuration or condition depicted in FIG. 5 (step 806). In this radially constricted condition, the flange member 10 has a diameter less than the diameter of the bore 204. In this condition, the distal end 22 of tubular body 14 may be partially or completely collapsed. The flange member 10 and the distal end 22 of retaining element 12 are passed through the bore 204 of the mounting ring 200 and through the hole in the heart wall 38, while leaving the proximal end 24 of the retaining element 12 outside of the heart and proximal to the mounting ring 200 (step 808). This may be done by positioning the tubular body 14 inside guiding tube 300 and pusher tube 304, with the flange member 10 disposed distal to the pusher tube 304, and advancing the guiding tube 300 through the mounting ring 200 until the distal end of the guiding tube 300 is just inside the heart, i.e., just past the interior surface the heart wall as depicted in FIG. 5. The stop member 302 of the guiding tube 300 may engage the proximal side of the mounting ring body 202 to prevent excessive advancement of the guiding tube 300. The flange member 10 may be brought to its radially-expanded condition and positioned to overlie the interior surface of the heart wall 38. This can be done by advancing pusher tube 304 within the guiding tube 300, so as to push the flange member 10 out of the guiding tube 300 through its distal end. The inner surface of guiding tube 300 may have a low coefficient of friction with flange member 10 so as to allow the flange to easily slide through guiding tube 300.

When the flange member 10 is clear of the guiding tube 300, the flange member 10 transitions back to its radially-expanded condition. Stop member 302 on the pusher tube 304 may engage the pusher tube 304 and arrest the distal movement of the pusher tube 304 when the distal end of the pusher tube 304 reaches the distal end of the guiding tube 300. Once the annular washer 34 has been ejected from the guiding tube 300, the guiding tube 300 and pusher tube 304 may be removed by sliding them proximally relative to the mounting ring 200 and retaining element 12. The physician may, for example, manually grasp the retaining element 12 adjacent its proximal end and pull it proximally to seat the annular washer 34 against the interior surface. At this stage of the process, the apparatus 100 has the configuration shown in FIG. 1.

Figure 2:
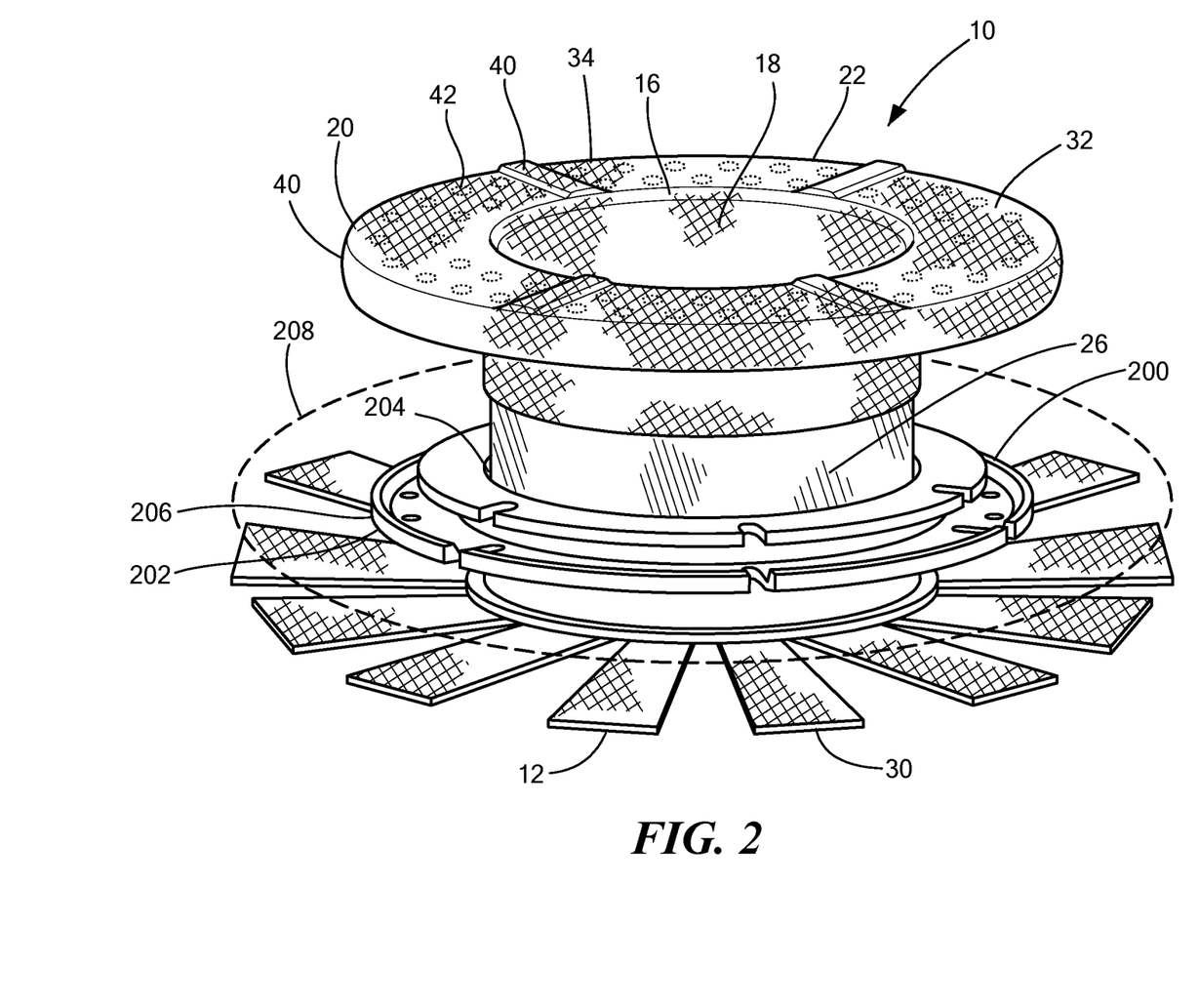
FIG. 2 is another perspective view of the apparatus of FIG. 1.

The proximal end 24 of the retaining element 12 may be separated into strips 30, by tearing along tear lines 28 (FIG. 4), and the strips 30 may be folded outwardly, away from the bore of the mounting ring 200, to the configuration depicted in FIG. 2 (step 812). In this condition, the retaining element 12 does may not protrude from the proximal end of the mounting ring 200. The physician may maintain the position of the flange member 10 within the heart by holding one or more of the strips 30. Alternatively, the physician may suture one or more of the strips 30 to the fabric ring 208 of the mounting ring 200, or to the exterior surface of the heart wall 38.

Figure 3:
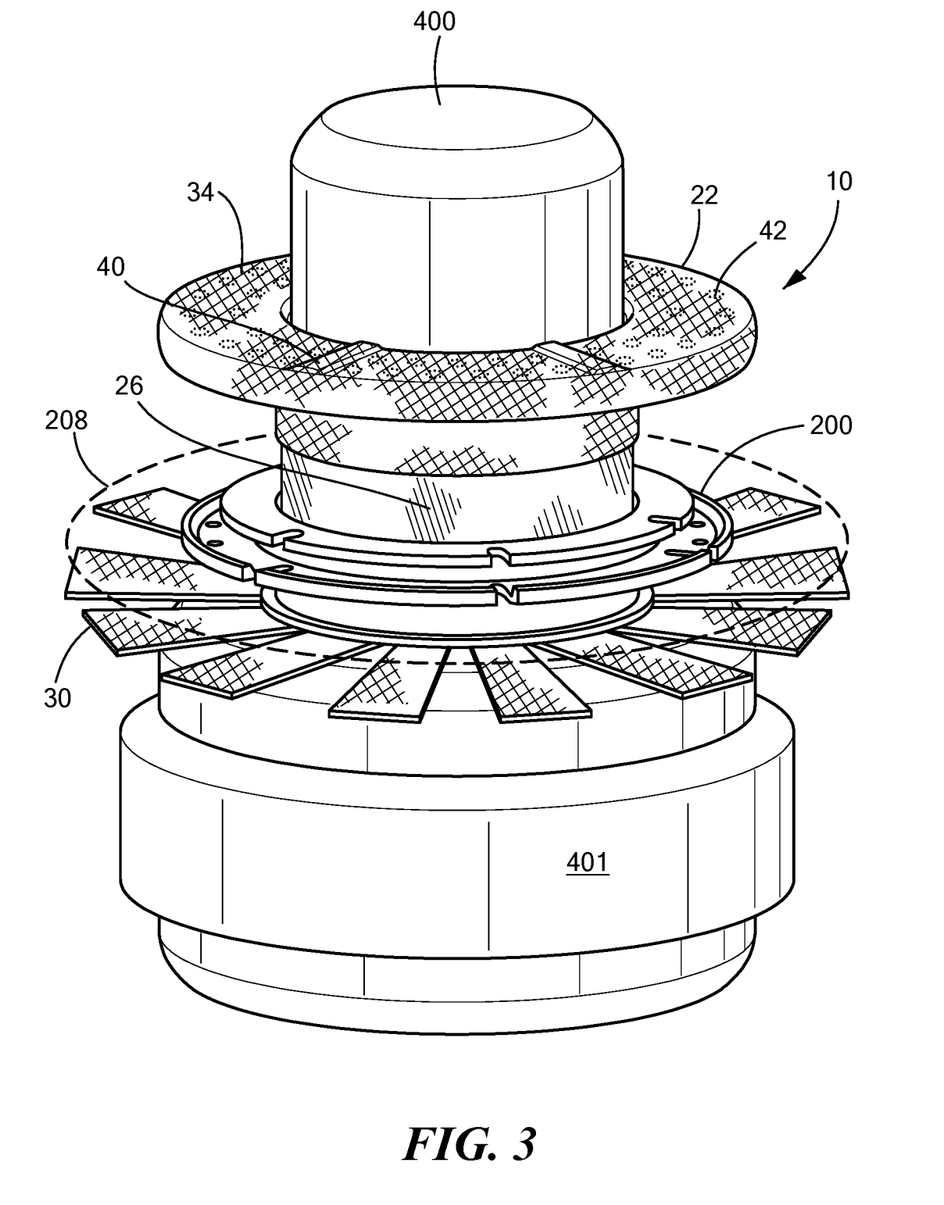
FIG. 3 is another perspective view of the apparatus of FIGS. 1 and 2 in conjunction with an MCSD.

An inlet element 400 (FIG. 3) of an MCSD 401, such as an inlet element or inflow cannula 400 of MCSD 401 may then be advanced into the opening of heart wall 38 through the bore 204 of the mounting ring 200 and inside of tubular body 14, until a portion of the inflow cannula 400 is disposed within the heart chamber (Step 814). The particular MCSD 401 depicted includes a centrifugal flow pump having a body with a rotor disposed therein and an elongated inlet element projecting from the body and having an inlet opening at its end remote from the body (FIG. 3). Because the tubular body 14 does not project proximally from the mounting ring 200, the pump may be advanced until body is proximate to or abutting the proximal side of the mounting ring 200, so that the assembly of the pump and mounting ring 200 forms a compact structure on the outside of the heart. At this stage, the wall of tubular body 14 resides between inlet member and mounting ring 200, as best appreciated with reference to FIG. 6. Once MCSD 401 is in place, clamp 210 is actuated to constrict the bore of mounting ring 200 so that at least a portion of mounting ring 200 is tightened around inflow cannula 400 to securing MCSD 401 into place relative to mounting ring 200 and relative to the heart (Step 816).

Prior to clamping mounting ring 200 onto inflow cannula 400, the apparatus 100 may move independently of mounting ring 200. However, when mounting ring 200 is clamped onto inflow cannula 400, tubular body 14 is secured into a fixed position between mounting ring 200 and inflow cannula 400. Thus, tubular body 14 may continue to maintain the position of flange member 10 against inner surface of heart wall 38. While flange member 10 and inflow cannula 400 are each positioned against opposite sides of heart wall, flange member 10 is not squeezing, or is only slightly squeezing, heart wall 38 against mounting ring 200. Because the mounting ring 200 is fastened to the heart wall 38 independently of the flange member 10, the flange member 10 need not bear forcibly on the inside of the heart wall 38 to hold the mounting ring 200 and MCSD 401 in place. By limiting the squeezing force that is applied to the heart wall 38 by flange member 10 and mounting ring 200, the potential for necrosis of heart tissue may be reduced. Once in position, flange member 10 may block heart tissues or deposits such as thrombus from entering the opening of the inflow cannula 400. In particular, the portion of heart wall 38 that flange member 10 directly overlies may be prevented from being drawn into opening 402 of inflow cannula 400 during operation of MCSD 401. Flange member 10 may also retard growth or deposition of tissue or thrombus around inflow cannula 400.

The apparatus and methods discussed above can be varied in numerous ways. For example, the flange member 10 can be brought to its radially constricted condition and advanced through the mounting ring 200 and through the opening in the heart wall 38 manually or with the use of tools other than the guiding tube 300 and pusher tube 304 discussed above. In a further variant, the mounting ring 200, the tubular body 14 or both can be provided with fasteners to hold the strips 30 in place temporarily from the time the strips 30 are folded over to the time the clamp 210 is actuated. For example, the ends of the strips 30 at the proximal end of the tubular body 14 may be provided with hook and loop fasteners and mating fasteners can be provided on the mounting ring 200. In another variant, the strips 30 may have sufficient stiffness such that they will remain in place once folded over the proximal end of the mounting ring 200, and the folded strips 30 may maintain position of the flange member 10 without any fastening. Conversely, the strips 30 may have sufficient length to extend beyond the area covered by the body of the MCSD 401, so that the physician can readily hold them while seating the MCSD 401 in the mounting ring 200.

The cored hole within heart wall 38 may be any diameter desired for affixing inflow cannula 402 of MCSD 401. For many MCSDs 401, the cored hole may be approximately 18 mm in diameter. As set forth above, flange member 10 may be configured so that it may be radially constricted to an extent that will allow flange member 10 to pass through the 18 mm diameter hole. Flange member 10 may also be configured so that once flange member 10 is in a position overlying inner surface of heart wall 38 that it will radially expand to a sufficient extent so as to prevent heart wall material from entering inlet opening 402. For example, flange member 10 may have a diameter of 35-40 mm or more in its radially expanded condition. The diameter of tubular body 14 may also vary depending on the dimensions of inflow cannula 400 and cored opening in heart wall 38. For example, if the cored opening in heart wall 38 is 18 mm the tubular body 14 may have a diameter around 18-20 mm.

Figure 7:
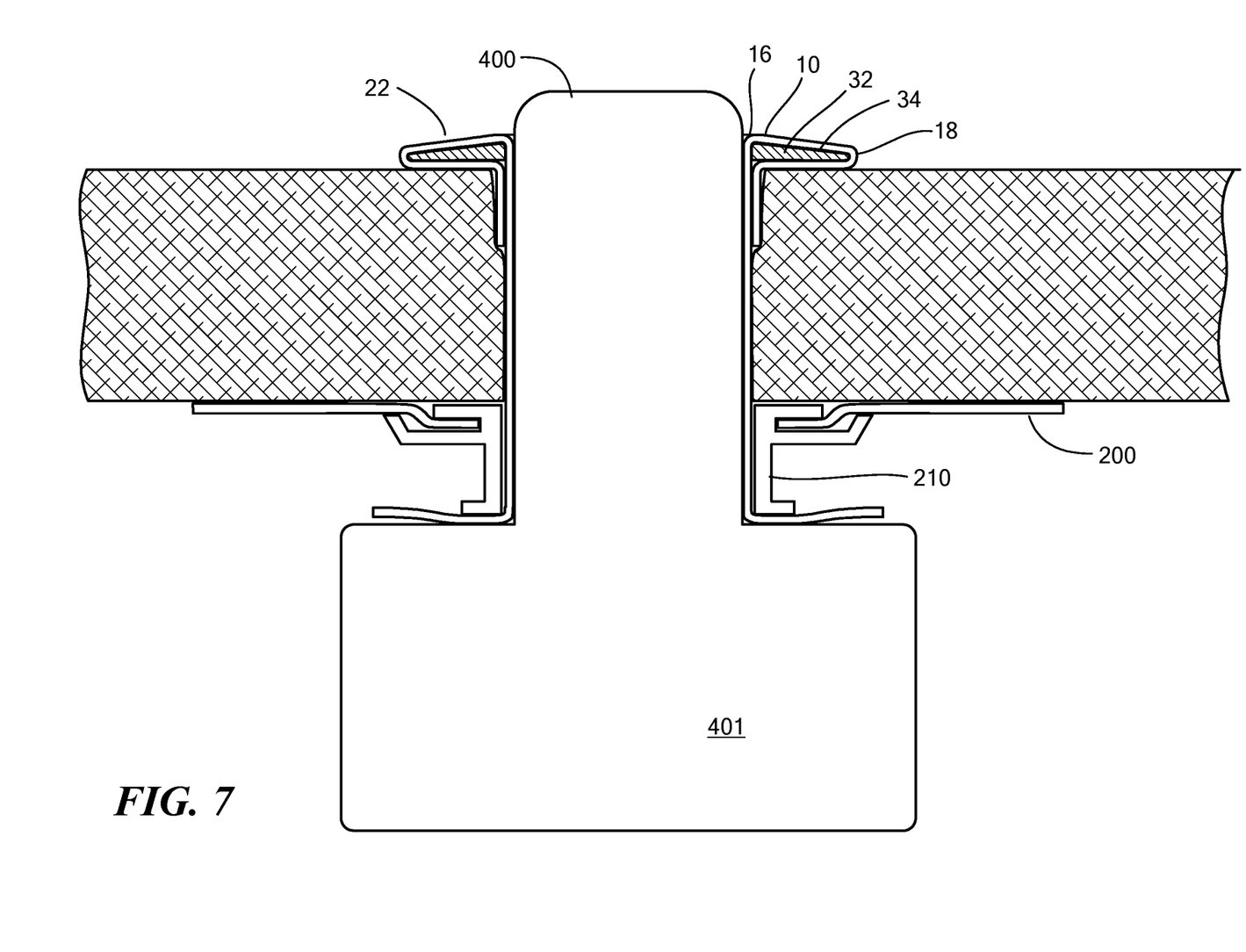
FIG. 7 is a cross-sectional view of another apparatus according to a further embodiment of the invention.

While FIGS. 1-6 show flange member 10 as having a circular shape of uniform thickness, flange member 10 may be configured to have any number of shapes in accordance with aspects of the disclosure. For example, FIG. 7 shows apparatus having a flange member 10 that varies in thickness in the radial direction, so as to decrease in thickness from inner edge 16 to outer edge 20. This variation in thickness may be configured so that flange member 10 may be more readily constricted in the radial direction during passage through the cored opening of heart wall 38. The flange member 10 may be have non-circular shape. For example, the flange member 10 in its radially-expanded condition may take the shape of a triangle, square, or multi-pointed star. The flange member 10 may also include a plurality of arms (not shown) that may be constricted radially so as to allow flange member 10 to pass through an opening of a heart wall, but which mechanically extend out radially from the flange member 10 after passage through the opening.

Returning to FIG. 1, tubular body 14 may be provided with any number of tear lines 28. For example, three or four tear lines 28 may be provided so as to create three to four strips 30. In addition, only some of the tear lines 28 may be torn during installation, so as to create fewer teardowns but wider strips 30. In addition, the flexible material of tubular body 14 may be covered in a lacquer (not shown), so as to stiffen the flexible material and allow for the tubular body 14 to maintain a given shape after placement within the heart wall 38. It is not essential to provide the tear lines 28 during manufacture; the physician may simply cut the tubular body 14 during installation to form the strips 30. In a further variant, the retaining element 12 such as the tubular body 14 may be crumpled axially or everted during installation so as to reduce projection of the tubular body 14 from the proximal end of the mounting ring 200. Additionally, a plurality of ribs 40 may be included on the flange member 10 and radially disposed about the opening 18. For example, as shown in FIG. 1, four ribs 40, which are composed of the same material as the flange member 10 may lend additional stiffness to the flange member 10 such that when the flange member 10 transition from the first radially constricted condition to the second radially expanded condition that the flange member 10 forms and maintain the desired radially expanded configuration. Additionally, the flange member 10 may define a plurality of apertures 42 extending through the flange member 10 to facilitate tissue ingrowth into the flange member 10. In the configuration shown in FIG. 1, the plurality of apertures are radially disposed about the flange member 10.

Different MCSDs 401 may be mounted. For example, the MCSD 401 may include an axial-flow pump having a generally tubular housing with an inlet end and an outlet end. The inlet end of such a housing may serve as the inlet element of the MCSD 401 which is inserted into the heart. Other MCSDs 401 include a pump which is mounted remote from the heart and an elongated, typically flexible, inlet cannula which serves as the inlet element of the MCSD 401. Where such an MCSD 401 is used, the tubular retaining element may continue to protrude proximally from the mounting ring. For example, the proximal end of the tubular element need not be formed into strips or folded over in the manner discussed above.

Figure 9:
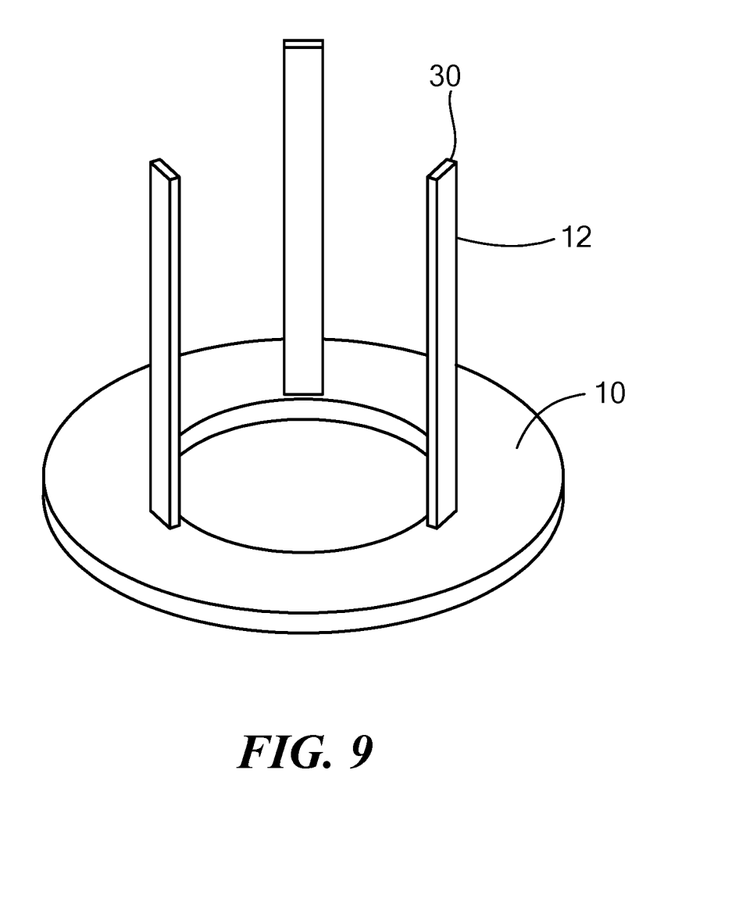
FIG. 9 is a diagrammatic perspective view of a component according to yet another embodiment of the application.

The retaining element 12 may be formed integrally with the flange member 10. In one configuration, the retaining element 12 may incorporate a check valve such (not shown) as a leaflet valve or duckbill valve to prevent loss of blood from within the heart prior to insertion of the inlet element of the MCSD 401. Such a check valve may be integral with the retaining element 12, and arranged to allow insertion of the inlet element 400 through the check valve. In yet another variant, the retaining element 12 is not tubular. For example, as shown in FIG. 9 the flange member 10 and a retaining element 12 may be in the form of plural discrete strips 30 extending proximally from the flange member 10.

Although the invention has been described above with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present disclosure. The following paragraphs further disclose certain aspects of the invention.

What is claimed is:

1. A method comprising:
advancing a flange member of the apparatus in a radially constricted configuration through an opening of a heart wall, the flange member including a retaining element defining a tubular body defining a proximal end and extending proximally out of the heart through the opening, the flange member being configured to transition to a radially expanded configuration after passage through the opening of the heart wall, the flange member further defining an annular pocket including a flexible annular washer disposed therein, the flexible annular washer including a ring-shaped polymeric member with a continuous outer edge about an outer perimeter of the ring-shaped polymeric member;
positioning the flange member and the retaining element to overlie an interior surface of the heart wall surrounding the opening;
advancing the inlet element through the opening of the heart wall and through the flange member to a position beyond the annular pocket and mounting the inlet element of the blood pump to the heart to prevent heart tissue from entering the inlet element;
tearing the tubular body into strips and folding the strips outwardly from the tubular body,
the tubular body being perforated to allow for tearing and including a flexible layer of material between the strips and the flange member, the flexible layer of material having a height greater than a thickness of the heart wall and an entirety of the flexible layer of material configured to prevent seepage of blood from the heart into an interior of the retaining element; and
connecting the strips to an exterior surface of the heart wall, the strips being configured to promote cardiac tissue ingrowth.

2. The method of claim 1, wherein mounting the inlet element includes fastening an independent mounting element on an exterior of the heart wall independently of the flange member.

3. The method of claim 2, wherein mounting the inlet element further includes engaging the mounting element with the retaining element to retain the inlet element in position relative to the mounting element and to retain the retaining element in position relative to the mounting element.

4. The method of claim 3, wherein fastening the mounting element to the heart is performed before advancing the flange member through the opening in the heart wall, and wherein the mounting element defines a bore, and wherein the flange member is advanced through the bore into the opening and the retaining element extends through the bore after advancement of the flange member through the opening.

5. The method of claim 4, wherein engaging the mounting element includes constricting the bore of the mounting element to retain the retaining element between the inlet element and the bore of the mounting element.

6. The method of claim 5, wherein advancing the flange member through the opening of the heart wall further includes:
placing the flange member within a guiding tube, the guiding tube having an open distal end;
advancing the open distal end of the guiding tube through the opening of the heart wall; and
advancing the flange member through the open distal end of the guiding tube.

7. The method of claim 1, wherein the flange member is resilient and biased in the radially expanded configuration.

8. The method of claim 1, wherein the flange member further includes:
an inner edge and the outer edge;
the inner edge defining an opening into the tubular body; and
the flange member decreasing in thickness from the inner edge towards the outer edge so that the flange member may be more readily constricted in a radial direction during passage through the opening of the heart wall.

9. The method of claim 1, wherein the flexible annular washer has a thickness between 2 millimeters (mm) and 3 mm.

10. The method of claim 1, wherein the flange member defines a plurality of radially disposed apertures extending through the flexible annular washer to facilitate tissue ingrowth into the flange member.

11. The method of claim 1, wherein the flexible annular washer has a uniform thickness between the outer edge and an inner edge of the ring-shaped polymeric member.

12. The method of claim 11, wherein the uniform thickness between the outer edge and an inner edge of the ring-shaped polymeric member is between 2 millimeters (mm) and 3 mm.

13. The method of claim 1, wherein the ring-shaped polymeric member has a continuous inner edge about an inner perimeter of the ring-shaped polymeric member.

14. The method of claim 1, wherein the ring-shaped polymeric member is composed of a polymeric material including at least one of rubber, polyethylene terephthalate (PET), or silicone.

15. The method of claim 1, wherein the flexible annular washer includes a plurality of ribs protruding from a surface of the ring-shaped polymeric member.

16. The method of claim 15, wherein the plurality of ribs are radially disposed about an opening defined by an inner edge of the ring-shaped polymeric member.

17. The method of claim 15, wherein the plurality of ribs are formed of the same material as the ring-shaped polymeric member.

18. The method of claim 15, wherein the plurality of ribs are configured to provide additional stiffness to the flange member such that when the flange member transitions from a first radially constricted condition to a second radially expanded condition, the flange member forms and maintain the second radially expanded configuration.

19. The method of claim 1, wherein the annular pocket is formed by a fabric.

20. A method comprising:

advancing a flange member of the apparatus in a radially constricted configuration through an opening of a heart wall, the flange member including a retaining element defining a tubular body defining a proximal end and extending proximally out of the heart through the opening, the flange member being configured to transition to a radially expanded configuration after passage through the opening of the heart wall, the flange member further defining an annular pocket sized to receive a flexible annular washer therein, the flexible annular washer including a ring-shaped polymeric member with a continuous outer edge about an outer perimeter of the ring-shaped polymeric member, and the tubular body including a portion that projects distally beyond the annular pocket;

positioning the flexible annular washer within the annular pocket;

folding the portion of the tubular body that projects distally beyond the annular pocket proximally within the tubular body to cover an inner edge of the flexible annular washer;

coupling the folded portion of the tubular body to an inner portion of the tubular body to retain the flexible annular washer within the annular pocket;

positioning the flange member and the retaining element to overlie an interior surface of the heart wall surrounding the opening;

advancing an inlet element of a blood pump through the opening of the heart wall and through the flange member to a position beyond the annular pocket and mounting the inlet element of the blood pump to the heart to prevent heart tissue from entering the inlet element;

tearing the tubular body into strips and folding the strips outwardly from the tubular body, the tubular body being perforated to allow for tearing and including a flexible layer of material between the strips and the flange member, the flexible layer of material having a height greater than a thickness of the heart wall and configured to prevent seepage of blood from the heart into an interior of the retaining element; and connecting the strips to an exterior surface of the heart wall, the strips being configured to promote cardiac tissue ingrowth.

* * * * *